(12) United States Patent
Tijsma et al.

(10) Patent No.: US 6,987,082 B2
(45) Date of Patent: *Jan. 17, 2006

(54) CONTROLLED RELEASE PRODUCTS AND PROCESSES FOR THE PREPARATION THEREOF

(75) Inventors: Edze Jan Tijsma, Maastricht (NL); Johannes Gijsbertus Antonius Terlingen, Landgraaf (NL); Saskia Haas-Schrijen, Kerkrade (NL); Hein Herman Vriesema, Bunde (NL)

(73) Assignee: OMS Investments, Inc., Los Angeles, CA (US)

( * ) Notice: Subject to any disclaimer, the term of this patent is extended or adjusted under 35 U.S.C. 154(b) by 28 days.

This patent is subject to a terminal disclaimer.

(21) Appl. No.: 10/684,162

(22) Filed: Oct. 10, 2003

(65) Prior Publication Data

US 2004/0069033 A1  Apr. 15, 2004

Related U.S. Application Data

(63) Continuation of application No. 09/795,840, filed on Feb. 28, 2001, now Pat. No. 6,656,882.

(51) Int. Cl.
*C05G 3/02* (2006.01)
(52) U.S. Cl. .................. 504/101; 71/28; 71/31; 71/64.02; 71/64.07; 424/400; 424/408; 424/409; 424/421; 523/132
(58) Field of Classification Search .............. 71/28, 71/64.02, 64.07, 31, 32, 49, 51; 424/405, 424/408, 409, 417, 421, 400; 504/101; 523/132
See application file for complete search history.

(56) References Cited

U.S. PATENT DOCUMENTS 3,223,518 A  12/1965  Hansen 4,019,890 A  4/1977  Fujita et al.

(Continued)

FOREIGN PATENT DOCUMENTS

EP  0731067  *  9/1996

OTHER PUBLICATIONS

Al-Zahrani Utilization of Polyethelene-,□□□□Ind. Eng. Chem. Res. 2000, 39, pp367-371.*

*Primary Examiner*—Neil S. Levy
(74) *Attorney, Agent, or Firm*—Jones Day

(57) ABSTRACT

A controlled release product is provided having a suppressed initial release period and a predetermined longevity. The product includes a particulate water soluble core material and a semi-permeable coating layer applied on the core material for controlling the release rate of the core material. The semi-permeable coating layer is formulated in accordance with the following equation to provide a release rate wherein initial release of core material from the product is suppressed so that less than about 15 weight percent of core material is released from the product within a 24 hour period after application of the product and wherein longevity of release, at ambient temperature, between the time of application and the time at which at least about 75 weight percent of the core material is released from the product is 60 days or less:

$$WVTR = \frac{\phi \cdot \delta}{\pi d^2}$$

wherein:
(i) WVTR is the water vapor transmission rate of the semi-permeable coating expressed in grams·$\mu$m/meters$^2$·day;
(ii) $\phi$ is the water diffusion rate (water flux) through the semi-permeable coating expressed in grams/day;
(iii) $\delta$ is the thickness of the coating layer expressed in $\mu$m; and
(iv) d is the average diameter of the particulate core material expressed in meters.

14 Claims, 2 Drawing Sheets

U.S. PATENT DOCUMENTS

| | | |
|---|---|---|
| 4,387,849 A | 6/1983 | Van Loveren et al. |
| 4,636,242 A | 1/1987 | Timmons |
| 4,657,576 A | 4/1987 | Lambie |
| 4,969,947 A * | 11/1990 | Moore .......................... 71/28 |
| 5,186,732 A | 2/1993 | Thompson et al. |
| 5,219,465 A | 6/1993 | Goertz et al. |
| 5,652,196 A | 7/1997 | Luthra et al. |
| 5,993,505 A | 11/1999 | Tijsma et al. |

* cited by examiner

CONTROLLED RELEASE PRODUCTS AND PROCESSES FOR THE PREPARATION THEREOF

BACKGROUND OF THE INVENTION

This application is a continuation application of U.S. application Ser. No. 09/795,840, filed Feb. 28, 2001 now U.S. Pat. No. 6,656,882.

TECHNICAL FIELD

The present invention relates to controlled release products such as controlled release fertilizer products. More particularly, it relates to coated products in particulate form which are structured to provide release profiles wherein initial release of active ingredients such as fertilizer nutrients therefrom is suppressed or inhibited for a predetermined period and longevity for release the active ingredients is within a period of time of 60 days or less after the time of application. The invention further relates to the use of such products, particularly, as potting soil starter fertilizers and to processes for producing particulate products exhibiting the desired release profiles.

BACKGROUND ART

The use of controlled release products such as controlled release fertilizer compositions to provide nutrients in growing media has been well known for a long period of time heretofore. Also, it has been known heretofore that the presence of additional nutrients in growing media may be beneficial depending on when these additional nutrients are made available to the plants growing in these media. However, the availability of too many nutrients can be detrimental to the plants. Furthermore, the presence of too much available nutrients can be considered not only an inefficient use of fertilizer, but also a threat to the environment.

Thus, it has been recognized previously that delivery of the correct amount of nutrients at the correct time is crucial for growing plants. However, with conventional water-soluble fertilizers optimal delivery of nutrients can only be achieved by employing very labor intensive methods. Alternatively, correct delivery of nutrients for nutrient uptake by plants can be achieved by modification of the fertilizer products such as by chemical means to reduce the solubility of the nutrients, or by physical means such as by coating or encapsulating the fertilizer compositions.

Likewise, it has been recognized heretofore that the controlled release of other water soluble core materials such as insecticides, herbicides, fungicides, pheromones, biostimulants, growth regulators and the like within a predetermined time period would be advantageous from a utilitarian and commercial standpoint.

With specific regard to coated or encapsulated fertilizers, such products are known to be very effective sources for providing controlled release of nutrients for growing of plants. In such products, the nutrients are released at controlled rates, resulting in sustained feeding of plants treated with the fertilizer. As a result, a single application of these so-called controlled release fertilizers (CRFs) can provide the necessary nutrients that would take multiple applications of soluble fertilizers.

The types of coatings that may be applied to soluble core materials such as fertilizer particles to produce CRFs include impermeable coatings, impermeable coatings with tiny pores, and semi-permeable coatings. Typical examples of CRFs with an impermeable coating are sulfur-coated fertilizers such as those disclosed in U.S. Pat. No. 4,636,242. With such sulfur-coated fertilizers, the release of nutrients from the sulfur-coating occurs by diffusion through imperfections in the sulfur coating and through coating breakdown followed by a relatively rapid release of nutrients.

Polymer/sulfur-coated fertilizers such as those disclosed in U.S. Pat. Nos. 5,405,426 and 5,219,465 are hybrid products that utilize a primary or inner coating of sulfur with a secondary or outer polymer coating. The nutrient release mechanism in such products results from a combination of water diffusion through the polymer coating and subsequently water penetration through the defects in the sulfur coating. Thus, the release properties of such polymer/sulfur-coated fertilizers are more uniform, and approach those of polymer-coated fertilizers, but at a reduced cost.

Polymer-coated fertilizers are considered to present a more technically advanced approach for controlling the release characteristics. Polymer coatings for soluble nutrient sources may be either impermeable coatings with tiny pores or semi-permeable coatings. The addition of a special surfactant to an impermeable coating material results in microscopic pores. Water diffuses through these pores into the core fertilizer granule dissolving the nutrients. The amount of surfactant in the coating determines its porosity and as a result its release characteristics (typical examples of these CRF products are sold with the trademark Nutricote®). It should be noted that, although these products cover a wide time period of release (from 40 days up to 12 months), these type of CRFs have the disadvantage that they always require the addition of a special compound in order to achieve the desired release profiles.

Semi-permeable polymeric coatings used for coating CRFs can be categorized as based either on thermoplastic (such as disclosed in U.S. Pat. Nos. 4,019,890 and 5,186,732) or on thermosetting (such as disclosed in U.S. Pat. Nos. 3,223,518 and 4,657,576, and sold with the trademark Osmocote®) resins. The presence of a polymeric coating on CRFs allows for a rather uniform and consistent nutrient release, provided that the barrier properties of the coating are sufficient. In such products, the release essentially is determined by the coating thickness alone. With some polymer-coated fertilizers, a relatively high initial rate of nutrient release is observed within the first 24 hours after application which is followed by a decreasing nutrient release rate for an extended period thereafter.

The application of a second polymeric coating may compensate for the high initial release rate, thus resulting in CRF products exhibiting delayed release (such as disclosed in U.S. Pat. No. 5,652,196). The most technically advanced state of the art in CRFs with delayed release characteristics comprises single layer coated products (such as disclosed in U.S. Pat. No. 5,993,505). The latter compositions are structured to provide a cumulative release of nutrients of less than 10% of the total nutrients within 30 days after exposure to moisture.

A general characteristic of the presently available commercial CRF products with semi-permeable coatings, such as the Osmocote® type products, is that these products provide a controlled release of nutrients for relatively long periods of time. Although the release rate of the nutrients out of the CRF products depends on several factors, the only one presently being used in practice to control the length of the release is the amount of coating. The generally accepted method of producing CRF products with different release periods is by using a coating material with high barrier properties at varying coating amounts or thicknesses.

The CEN (Comité Européen de Normalisation) TC 260/ WG 4/Task Force (hereinafter referred to as "the CEN TC 260) has provided a standard definition for controlled or slow-release fertilizers. Under that definition, a product may be considered a CRF if the release profile of the product meets the following criteria:

(1) No more than 15 weight percent (wt. %) of core material is released from the fertilizer product within the first 24 hours after application of the product, at ambient temperature;

(2) No more than 75 weight percent (wt. %) of core material is released from the fertilizer product within 28 days after application of the product, at ambient temperature; and (3) At least 75 weight percent (wt. %) of core material is released from the fertilizer product within a predetermined release time after application, at ambient temperature.

With regard to criterion 1 above, it should be noted that this standard is applied to all of the controlled release products of the present invention in defining the suppressed or inhibited initial release characteristics thereof. Concerning criterion 3 above, it should be further noted that for purposes of the present invention, the predetermined release time after application, at ambient temperature, of the controlled release products is 60 days or less. Therefore, the term "longevity" as employed herein defines the time period of 60 day or less between the time of application of core material from the product and the time at which about 75 weight percent (wt %) of the active ingredients such as fertilizers, insecticides, herbicides, fungicides, pheromones, biostimulants, growth regulators and the like and mixtures thereof is released.

A recognized shortcoming of presently available CRF products with semi-permeable coatings is that, as a result of the focus on using coatings with high barrier properties, the range of CRF release periods provided by these products covers release periods from 60 days up to 18 months at ambient temperatures, depending only on the amount of coating applied. In such cases, as soon as sufficient coating material is applied to adequately cover the fertilizer granules (which in general is the case after applying lower coating weights, such as 5 wt. % of coating), the resulting product will exhibit a longevity of more than 60 days from the time of application of the product to a plant, at ambient temperatures, as a result of the barrier properties of the coatings employed. However, if the amount of such coating applied is decreased in an attempt to reduce the longevity of the products below 60 days, it has been found that insufficient coating material is provided to adequately cover the granules and a significant amount of imperfectly coated granules are created. Consequently, these granules release too many nutrients in the first few days, rendering such coated product unsuitable for controlled release products.

Thus, there has been a need heretofore for fertilizer products which have semi-permeable coatings and which have a longevity of 60 days or less and meet the criteria for the fertilizer to be considered a CRF as defined by the CEN TC 260 standard, particularly, in terms of criteria 1 and 2 set forth above. For example, under criterion 1, initial release of not more than 15 wt. % of core material from the product would have to occur within 24 hours after application and under criterion 2 for a a product to be classified as a CRF, as defined by CEN TC 260, the shortest longevity of the fertilizer product would have to be 28 days since not more than 75 wt. % of core material could releases from the product within 28 days after application. No fertilizer products have been known, heretofore, that comply with criteria 1 and 2 set forth under the CEN TC 260 standard when combined with criterion 3 when the predetermined period thereunder is 60 days or less.

Furthermore, in addition to fertilizer products, it should be recognized that no controlled release products have been known heretofore which exhibit release profiles wherein water soluble core materials such as insecticides, herbicides, fungicides, pheromones, biostimulants, growth regulators and the like are released at a rate such that initial release of core material from the product is suppressed so that less than about 15 wt % of core material is released from the product within a 24 hour period after application of the product and wherein longevity of release, at ambient temperature, between the time of application and the time at which at least about 75 wt % of the core material is released from the product is 60 days or less

DISCLOSURE OF THE INVENTION

It is a principal object of the present invention to provide controlled release products which display specific release profiles and, particularly, to coated products such as fertilizer products which exhibit release of active ingredients (such as nutrients) within a relatively short period of time (longevity less than 60 days) in combination with a suppressed initial release period. A further principal object of this invention is to provide processes for producing such controlled release products.

Another important object of the invention is to provide controlled release products such as fertilizer products which exhibit a longevity ranging between about 1 day and 60 days, preferably between about 28 and about 49 days but, also, less than 28 days.

A further significant object of the invention is to provide a controlled release fertilizer product having particulate nutrient core material encapsulated in a semi-permeable coating layer wherein the product exhibits a release profile wherein initial release of core material from the product is suppressed so that less than about 15 weight percent of core material is released from the product within a 24 hour period after application of the product and wherein longevity of release, at ambient temperature, between the time of application and the time at which at least about 75 weight percent of the core material is released from the product is 60 days or less.

A still further object is to provide controlled release products having the above described characteristics which are adapted for use as potting soil starter fertilizers.

Accordingly, a controlled release product in accordance with the present invention exhibits a suppressed initial release period and a predetermined longevity of 60 days or less. Such a product comprises:

(a) a particulate core material comprising at least one water soluble composition selected from the group consisting of fertilizers, insecticides, herbicides, fungicides, pheromones, biostimulants, growth regulators and mixtures thereof; and (b) a semi-permeable coating layer applied on the core material for controlling the release rate of the core material;

(c) the semi-permeable coating layer being formulated in accordance with the following equation to provide a release rate wherein initial release of core material from the product is suppressed so that less than about 15 weight percent of core material is released from the product within a 24 hour period after application of the product and wherein longevity of release, at ambient temperature, between the time of application and the time at which at least about 75 weight percent of the core material is released from the product is 60 days or less:

$$WVTR = \frac{\phi \cdot \delta}{\pi d^2}$$

wherein:

(i) WVTR is the water vapor transmission rate of the semi-permeable coating expressed in grams·$\mu$m/meters$^2$·day;

(ii) $\phi$ is the water diffusion rate (water flux) through the semi-permeable coating expressed in grams/day;

(iii) $\delta$ is the thickness of the coating layer expressed in $\mu$m; and (iv) d is the average diameter of the particulate core material expressed in meters In a preferred embodiment of the invention, it has been found that one or more of the above-identified objects and others, can be accomplished by utilizing specific coating material having a water vapor transmission rate (WVTR) preferably, greater than about 800 g·$\mu$m/m$^2$·day; and most preferably, greater than about 900 g·$\mu$m/m$^2$·day (for example, employing a coating based on a modified cyclo oil alkyd resin); and applying the coating material at a coating thickness of about 20 to about 110 $\mu$m.

BEST MODE FOR CARRYING OUT THE INVENTION

The present invention relates to controlled release products including CRF products having a suppressed initial release period and a longevity of 60 days or less, including products with a longevity of less than 28 days.

In particular, the present invention is based (at least in part) on the interaction between the WVTR of a coating material applied on particles or granules such as fertilizer particles or granules and the release performance or release profile exhibited by the resulting coated products. That is, the invention is based on the principle equation which relates the water diffusion $\phi$ (water flux) through a coating applied on particles or granules such as fertilizer particles or granules to WVTR as follows:

$$WVTR = \frac{\phi \cdot \delta}{\pi d^2}$$

wherein:

WVTR is expressed in grams·$\mu$m/meters$^2$·day;

$\phi$ represents the water flux (expressed in grams/day), $\delta$ represents the thickness of the coating applied (in $\mu$m); and d represents the diameter of the fertilizer granules (in meters).

Other factors which optionally may also be considered in determining optimal release characteristics of a particular controlled release product of this invention on the basis per day release of core material include fixed parameters such as the solubility and morphology of the core material itself.

In practice, a simulation program (in Visual Basic) using an iterative model based on the foregoing equation is used for determining the desired release performance of a particular controlled release product of this invention. Accordingly, the release profile of the products can be calculated for any combination of WVTR, granules size and coating thickness. For example, employing this methodology, it has been determined that for fertilizer granules with a diameter between 2 and 3 mm (i.e., 0.002–0.003 meters) the WVTR should range between 800 and 3000 g·$\mu$m/m$^2$·day for obtaining preferred CRF products of the present invention at practical coating thicknesses of between about 20 and about 110 $\mu$m.

In determining minimum coating amounts to be employed in obtaining adequately coated or encapsulated fertilizer granules herein, it has been found that several factors should be considered including coating formation, fertilizer granule sphericity and morphology. For typical coatings being applied as fertilizer coatings and for typically sized fertilizer granules, it has been determined that the preferred minimum coating weight should be about 5 wt. %, corresponding to a coating thickness of about 20 $\mu$m.

The present invention contemplates both new controlled release products including fertilizer products and processes to make these products. As with many controlled release products, the products of this invention comprise a core of water soluble agent. Such cores are obtained in granular or prilled form.

Generally, the fertilizer products of this invention comprise a nutrient core and an encapsulating semi-permeable coating. Thus, when the present invention is used for fertilizer products, the granular core material to be employed for producing such fertilizers may comprise any type of fertilizer core compound(s).

Known chemical fertilizers suitable for use as core materials herein include ammonium sulfate, potassium nitrate, potassium sulfate, urea, ammonium nitrate, monopotassium sulfate, ammonium phosphate, super-phosphate, dicalcium phosphate, basis calcium phosphate, potassium phosphate, potassium chloride, magnesium oxide, magnesium sulfate and the like or any fertilizers obtained from compounding a mixture of these fertilizers.

In a preferred embodiment of this invention, the core comprises at least one secondary nutrient and/or micronutrient. Suitable secondary nutrients include calcium, magnesium, sulfur and mixtures thereof. Suitable micronutrients, in chelated or non-chelated form, include iron copper, zinc, manganese, boron, cobalt, chlorine, sodium, molybdenum and mixtures thereof.

Furthermore, the core material may comprise insecticides, herbicides, fungicides, pheromones, biostimulants, growth regulators and the like and mixtures thereof. For instance, one or more suitable herbicides for use in the present invention include 2,4-dichlorophenoxyacetic acid, 3,6-dichloro-2-pyridinecarboxylic acid; 3,6-dichloro-o-anisic acid, 6,7-dihydrodipyrido (1,2-a:2',1'-c)pyrazinediium dibromide; N-(phosphonomethyl)glycine, (2-[4,5-dihydro-4-methyl-4-(1-methylethyl)5-oxo-1H-imidazo-2-yl]-3-pyridinecarboxylic acid); methyl 2-[[[[(4-methoxy-6-methyl-1,3,5-triazin-2yl)amino] carbonyl]amino]sulfonyl]benzoate; 5-tert-butyl-3-(2,4-dichloro-5-isopropoxyphenyl)-1,3,4-oxadiazol-2(3H)-one; N-(1-ethylpropyl)-3,4-dimethyl-2,6-dinitrobenzenamine, ehtyl 2-chloro-5-4-chloro-(5-difluoromethoxy)-1-methyl-1H-pyrazol-3-yly-4-fluorophenoxyacetate, 3-7, dichloro-8-quinolinecarboxylic acid, 3,5,6-trichloro-2-pyridinyloxyacetic acid, glyphosates, glufosinate-ammonium, derivatives of phenoxyacetic acid, phenoxypropionic acid, phenoxybutyric acid, 4-amino-3,5,6-trichloro-picolinic acid, phenoxyethyl sulphuric acid, halogeneated benzoic acid, halogenated acetic acid, halogenated propionic acid, phenylurea, or bipyridylium, and certain mineral salts of sodium chlorate, sodium or potassium 2,4-dichlorophenoxy acetate, sodium or potassium 4-chloro-2-methylphenoxyacetate, sodium or potassium 2,4,5-trichlorophenoxyacetate, sodium or potassium 2-(4-chloro-2-methylphenoxy)-propionate, sodium or potassium 2-(2,4-dichlorophenoxy)-propionate, sodium or potassium 4-(2,4-dichlorophenoxy)-butyrate, sodium or potassium 4-(4-chloro-2-methylphenoxy)-butyrate, sodium or potassium 4-(2,4,5-trichlorophenoxy)-butyrate, sodium or potassium 4-amino-3,5,6-trichloropicolinate, sodium 2-(2,4-dichlorophenoxy)-ethylsulfate, 2,3,6-trichlorobenzoic acid, 3,6-dichloro-2-methoxybenzoic acid, sodium chloracetate, trichloracetic acid, sodium 2,2-dichloropropionate, sodium 2,2,3-trichloropropionate, N,N-dimethyl-N'-phenyl urea and its trichloracetic salt, the trichloracetate of N,N-dimethyl-N'-(4-chlorophenyl) urea, copper suphate, iron sulphate, 1,1'-dimethyl-4,4'-bipyridylium dichloride, 1,1'-bis(3,5-dimethyl-4-morpholinyl)-carbonylmethyl-4,4'-bipyridylium dichloride, 9,10-dihydro-8α, 10α-diazaphenanthrene dibromide, 3-amino-1,2,4-triazole, and the like and mixtures thereof including symmetrical triazines falling under the formula:

in which X is chlorine, methoxy or methylthio $R_1$, $R_2$, $R_3$ and $R_4$ are the same or different and are each hydrogen or an alkyl residue containing 1–5 carbon atoms in branched or straight chain and optionally bearing a methoxy group.

Suitable insecticides for use in the present invention include O,S-dimethyl acetylphosphoramidothioate; (E)-N-[(N-{(6-chloro-3-pyridinyl)methyl] -N'-cyano-N-methyl-ethanimidamide; hydrazinecarboxylic acid, 2-{4-methoxy [1,1'-biphenyl}-3-yl)-, 1-methylethyl ester; [1.alpha., 3.alpha.-(Z)]-(.±-.)-(2 methyl{1,1'-biphenyl}-3-yl)methyl 3-(2-chloro-3,3,3-trifluoro-1-propenyl)-2,2-dimethylcyclopropanecarboxylate; 1-naphthyl-N-methylcarbamate; 4-bromo-2-(4-chlorophenyl)-1-ethoxymethyl-5-trifluoromethylpyrrole-3-carbonitrile; (S)-cyano( 3-phenoxyphenyl) methyl (S)-4-chloro-alpha-(1-methylethyl)benzeneacetate, 5-amino-1-(2,6-dichloro-4-(trifluoromethyl)phenyl)-4-(1,R,S)-(trifluoromethyl)sulfinyl)-1-H-pyrazole-3-carbonitrile; benzoic acid, 4-chloro-, 2-benzoyl-2-(1,1-dimethylethyl)hydrazide; pyrethrins; oxadiazin-4-imine, 3-(2-chloro-5-thiazolyl)methylytetrahydro-5-methyl-N-nitro and the like and mixtures thereof.

Suitable fungicides for use in the present invention include methyl (E)-2-{2-[6-(2-cyanophenoxy)pyrimiidin-4-yloxy]phenyl}-3-methoxyacrylate; tetrachloroisophthalonitrile; 5-ethoxy-3-(trichloromethyl)-1,2,4-thiadiazole; 1-[[2-(2,4-dichlorophenyl)4-propyl-1,3-dioxolan-2-yl]methyl]-1H-1,2,4-triazole; carbamic acid, 2-1-(4-chlorophenyl)-1H-pyrazol-3-ylyoxyymethylyphenyllymethoxy-, methyl ester; dimethyl 4,4-o-phenylenebis-(3-thioallophanate) and the like and mixtures thereof.

Suitable plant growth regulators for use in the present invention include [(2RS,3RS)-1-(4-chlorophenyl)-4,4-dimethyl-2-(1,2,4-triazol-1-yl)pentan-3-ol]; [α-(1-methylethyl)-α[4-(trfluoromethoxy)phenyl]-5-pyimidine-methanol]; 4-(cyclopropyl-alpha-hydroxy-methylene)-3,5-dioxo-cyclohexane-carboxylic acid; and the like and mixtures thereof.

The semi-permeable coating material to be applied on the core material in the present invention can be based on any kind of material, thermoplastic or thermosetting, which is able to form a uniform continuous polymer film with a desired WVTR, preferably, greater than 800 g·μm/m²·day. In a more preferred embodiment, the polymer film has a WVTR higher than 900 g·μm/m²·day.

In the present invention, suitable thermoplastic coating materials may comprise vinyl resins such as poly(vinyl acetate), poly(vinyl alcohol), poly(vinyl chloride), poly(vinylidene chloride), poly(vinyl pyrrolidone), poly(vinyl acetal), poly(vinyl methylacetamide); polyolefines such as polyethylene, polypropylene, polyisobutylene; styrene-based polymers; acrylic polymers; polyesters such as poly(alkylene terephthalate), poly(caprolactone); poly(oxy alkylene)s, such as poly(ethylene oxide), poly(propylene oxide); cellulose derivatives, such as celluloseacetate; polyamides; polyamines; polycarbonates; polyimides; polysulfones; polysulfides; and polysaccharides.

In the present invention, suitable thermosetting coating materials may comprise polyesters such as alkyds or modified alkyds; epoxy resins; urethane resins; and aminoplastics. The coating is preferably a dicyclopentadiene ("DCPD") polymeric product (containing either linseed oil or an alkyd resin based on a soybean oil) such as OSMOCOTE® resin commercially available from The Scotts Company.

Optionally the coating may comprise non-specific additives (inert fillers), such as talc. The coating material may be applied from a solution, or from dispersion. When applied from a solution, use of a solvent in which the resin dissolves at all temperatures is preferred, thus, making it possible to use resin solutions having a relatively high solids content (more than 40% by weight).

Preferably, the semi-permeable coating material is constructed in such a manner that it meets the following functional criteria:

(a) possesses good coat-forming properties on particles or granules such as fertilizer granules (e.g., viscosity, curing capacity);

(b) resulting in a coating with good mechanical properties (e.g. flexibility), (c) yielding a non-toxic coating, and (d) resulting in a coating with good stability towards typical end-user conditions (e.g. temperature).

Present commercially available CRF products make use of semi-permeable coatings applied at various amounts to obtain products with various longevities. These CRF products employ coatings with low WVTR, which enables the manufacture of CRF products with a release period from 60 days up to 18 months, depending on the amount of coating applied. As soon as sufficient coating material is applied to adequately cover the fertilizer granules, the resulting CRF product exhibits a longevity of at least 60 days due to the high barrier properties (i.e. low WVTR) of the coating applied.

However, by lowering the amount of coating applied, insufficient coating material is provided to cover the granules, and the resulting product does not display controlled release from the standpoint of initial release characteristics within the first 24 hours after application. Thus, instead of making a CRF product with short longevity, a product lacking initial controlled release properties is obtained. Heretofore, no CRF products with semi-permeable coatings have been known which provide a longevity shorter than 60 days.

The present invention uses the WVTR of a coating material to reach a specific longevity. We have found that coatings, which display a specific WVTR, when applied as an encapsulating agent on fertilizer granules, result in CRF products having a desired specific longevity. Thus, instead of randomly using any coating with high barrier properties (e.g., with a relatively low WVTR, of lower than about 800 g·$\mu$m/m$^2$·day) and applying it in a specific amount, the present invention employs a coating material with a high WVTR to be applied at a specific coating level. In a preferred embodiment of this invention, a coating material is used having a WVTR higher than 800 g·$\mu$m/m$^2$·day and this coating material is applied on a core material to provide a CRF product which displays a suppressed or inhibited initial release within the first 24 hours after application with a longevity of 60 days or less.

As a result of their favorable performance as barrier materials, polymers have been gaining wide use in coating applications. Barrier properties, such as the WVTR, are directly related to the chemical composition of the polymeric material. By influencing the chemical composition of the polymer backbone a polymer with a specific WVTR can be obtained. The rate of permeation of liquids, in particular water, through polymer coatings has been extensively studied over many years, mainly within the field of packaging films and protective coatings on e.g. wood. Based on the results of these studies, methods can be developed to change, in particular to increase, the WVTR of polymeric materials. For example, introduction of hydrophilic segments by means of chemical reaction is a method that can be employed to increase the WVTR of a polymeric material. Alternatively, introducing less crosslinking sites into a polymer results in a less dense polymer coating, and hence a coating with a higher WVTR.

The test employed herein for purposes of determining the WVTR of coating materials complies with the standard test method for determining moisture vapor permeability of organic coating films (ASTM E96). This test method involves a permeability cup that can be weighed and permits the exposure of the coating film under test to a condition of high humidity on one side, and of low humidity on the other side. A film of the coating material under test is fastened over the mouth of the cup, which contains water. The cup is weighed at intervals and the results are used to calculate the rate of water vapor movement through the film.

The present invention makes use of the WVTR (in gram of water times $\mu$m film thickness per m$^2$ film area per day) of a specific coating material as determined by the herein described equation. The WVTR is a property of a coating material which is determined by the chemistry of the material. Therefore, any individual coating material displays its specific WVTR and, moreover, any (chemical) modification with respect to the coating material has an impact on the WVTR. WVTR determinations have been used in literature on a variety of coatings to demonstrate the effect of specific formulations.

Optionally, the coating material may contain non-specific additives (inert fillers), such as talc. The coating material may be applied from a solution or from a dispersion or by in situ reaction. When applied from a solution, use of a solvent in which the resin dissolves at all temperatures, is preferred. Furthermore, it is possible to use resin solutions having a relatively high solids content (more than 40% by weight).

The coating may be applied to the core material by a number of methods. However, in a most preferred embodiment of this invention, the coating process is performed in either a coating drum and/or a fluidized bed, such as a Würster column. The thickness of the coating applied on the particles or granules is, preferably, between 20 and 110 $\mu$m.

Coatings are applied onto soluble core materials such as fertilizer granules to control their rate of dissolution. The coating applied determines the water permeation into the granule and, thus, influences the release profile of the core material. Once the coating is disrupted and solute movement starts, nutrients become available, for example, to plants treated with the product. The present invention is based on the interaction between the WVTR of a coating material and the release of the nutrients out of the granule being encapsulated by the coating. Although not fully understood, the interaction is believed to enable the manufacture of CRF products that would otherwise not be attainable, in particular with respect to CRF products with longevities shorter than 60 days. Additionally, the interaction provides a novel approach in the development and the manufacture of CRF products in general to produce products demonstrating new release profiles or patterns.

For purposes of the present invention, it is preferred to employ core materials having relatively smooth surfaces. However, the invention is also useful for coating irregularly shaped particles and granules.

The following examples further illustrate details of the products and processes of the present invention. While the invention is described with preferred embodiments, it is to be understood that variations and modifications thereof may be resorted to as will be apparent to those skilled in the art. Such variations and modifications are to be considered within the purview and the scope of the claims appended hereto.

EXAMPLE 1

A series of test sample granular NPK fertilizers was prepared from fertilizer granules having an average diameter of 3 mm (i.e., 0.003 meters) and a composition of 17 wt. % N, 10 wt. % $P_2O_5$, and 13 wt. % $K_2O$. Furthermore, micronutrient trace elements (Fe, Mn, Zn, Cu, B and MgO) were present in the granules. These fertilizers particles are denoted herein as 17–10–13+.

The series of test samples was prepared from these fertilizer granules by placing the granules in a pilot rotating drum coater and heating the granules to a temperature of 80° C. After heating, separate solutions of coating resins (hereinafter designated as Resin A, Resin B and Resin C), in white spirit, were added to separate batches of heated granules by applying one of the separate resin solutions onto the rotating bed of granules. This addition of each of these resins was continued until a coating thickness of 33 µm was obtained on each of the coated particle samples. After coating, the fertilizer granules were cooled down to room temperature and the sample was ready for testing.

In this manner, a first test sample (herein after referred to as Sample A) was prepared by coating the granules with a coating resin (Resin A) comprising a so-called cyclo oil alkyd resin based on soybean oil (a coating composition available from The Scotts Company under the trade name SCR RM 1210) which may be considered representative of the coating material present on Osmocote® CRF products sold by the Scotts Company. A significant characteristic of this coating material was its relatively low WVTR and for purposes of this Example the coated product produced with this coating is considered to be a control or reference product.

Likewise, Sample C was prepared by coating the granules with a coating resin (Resin C) comprising a modified cyclo oil alkyd resin based on linseed oil (a coating composition available from The Scotts Company under the trade name SCR EP 9361), which was modified using less crosslinker, and therefore resulting in a coating with a relatively high WVTR and Sample B (a coating composition available from The Scotts Company under the trade name SCR RM 1310) was prepared by coating the granules with a coating resin (Resin B) comprising a mixture of Resin A and Resin C, blended in such a manner (50/50 blend by weight) that a coating was obtained with an intermediate WVTR.

The WVTR of the coating materials was determined according to the standard test method under ASTM E96. The WVTR of each of the three coating materials (Resin A, Resin B and Resin C), which were used to prepare the test samples (Sample A, Sample B and Sample C) employed in the test conducted under Example 2 herein are shown in the following Table 1:

TABLE 1

| Coating material | WVTR (g · µm/m² · day) |
|---|---|
| Resin A | 700 |
| Resin B | 900 |
| Resin C | 1200 |

EXAMPLE 2

The fertilizer products designated Sample A, Sample B and Sample C produced in accordance with the procedure described in Example 1 above were analyzed according to the so-called waterleach test at 21° C. For the waterleach test, 20 g samples of coated fertilizer were placed in 400 ml of water at 21° C. At certain time intervals the conductivity of the solution was measured and the water replaced by fresh water. Based on the measured conductivity the concentration of nutrients was calculated using appropriate calibration constants. These calibration constants are specific for a certain type of fertilizer and need to be determined experimentally. Alternatively, the release of nutrients can be determined by measuring the amount of nutrients present in the water by using standard chemical analytical methods.

Figure 1:
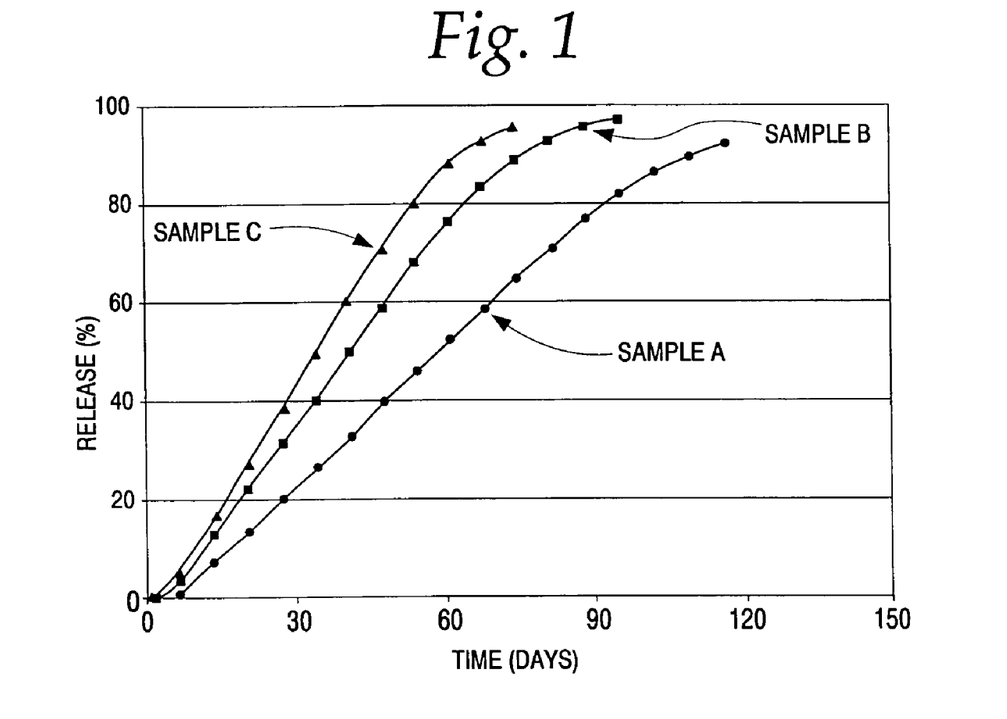
FIG. 1 illustrates a comparison of the nutrient release profile of a control sample (Sample A) of a standard coated 17-10-13+ fertilizer product encapsulated with Resin A prepared in accordance with Example 1; a 17-10-13+ fertilizer product of the present invention (Sample B) encapsulated with Resin B prepared in accordance with Example 1 herein; and a coated 17-10-13+ fertilizer product of the present invention (Sample C) encapsulated with Resin C prepared in accordance with Example 1 herein.

The cumulative release curves of the sample fertilizer products Sample A, Sample B and Sample C from Example 1 are illustrated in FIG. 1 wherein the longevity of the CRF products tested were shown to be 90 days for the control Sample A; 60 days for Sample B; and 50 days for Sample C and wherein the initial release period was suppressed or inhibited so that less than 15% wt % of core material is released within the first 24 hour period after application to a plant.

Thus, it can be seen that products produced in accordance with the present invention (Sample B and Sample C) exhibit longevity of 60 days or less while the control sample (Sample A) did not achieve this desired release rate in products which have the same thickness of coating applied on granules of the same average diameter.

EXAMPLE 3

This Example illustrates two types of semi-permeable coatings (thermosetting and thermoplastic) which may be employed in accordance with this invention to produce fertilizer products.

In Table 2, two resins designated Resin D and Resin E are shown with their corresponding WVTR (determined as described in Example 1). Resin D comprises an alkyd modified with (hydrophilic) silicone segments (a commercially available coating composition sold by Blagden Chemicals Ltd. under the trade name Blagden 1508) and Resin E comprises a copolymer based on ethylene and vinylalcohol (CAS Registry Number [25067-34-9]).

TABLE 2

| Coating material | Type | WVTR (g · µm/m² · day) |
|---|---|---|
| Resin D | Silicone-modified alkyd | 1800 |
| Resin E | Poly(ethylene/vinylalcohol) | 1500 |

EXAMPLE 4

This Example illustrates the use of the various types of semi-permeable coatings described herein for producing a series of test sample granular NPK fertilizers.

One of the test samples was prepared in accordance with the procedure described in Example 1 wherein an NPK (17-10-13+) fertilizer granule with an average diameter of 2 mm (i.e., 0.002 meters) was encapsulated with Resin A (described in Example 1) at a coating thickness of 36 µm. The resulting CRF product is identified herein as Sample A' and should be considered to be a control or reference product herein. Another test sample was prepared in accordance with the procedure described in Example 1 wherein an NPK (17-10-13+) fertilizer granule with an average diameter of 3 mm (i.e., 0.003 meters) was encapsulated with Resin A (described in Example 1) at a coating thickness of 39 µm.

The resulting CRF product is identified herein as Sample A" and should also be considered to be a control or reference product herein.

A further test sample (designated Sample D) was prepared in accordance with the procedure described in Example 1 wherein an NPK (17-10-13+) fertilizer granule with an average diameter of 2 mm (i.e., 0.002 meters) was encapsulated with Resin D (described in Example 3) at a coating thickness of 36 $\mu$m. Another test sample (designated Sample E) was prepared by encapsulating an NPK (17-10-13+) fertilizer granule having an average diameter of 3 mm (i.e., 0.003 meters) with was encapsulated with a dispersion of Resin E (described in Example 3) in a fluidized bed. A batch of the fertilizer granules was placed in a pilot-scale fluidized bed Würster-type column and preheated at 70° C. The dispersion was sprayed from the bottom of the bed until a coating thickness of 39 $\mu$m was obtained. After coating the fertilizer was cooled down to room temperature.

EXAMPLE 5

Figure 2:
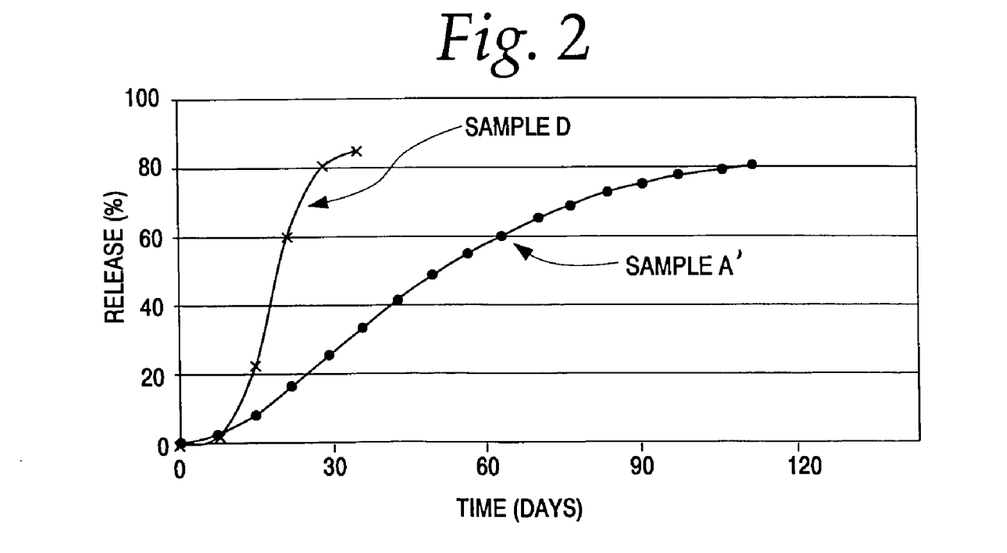
FIG. 2 illustrates a comparison of the nutrient release profile of a control sample (Sample A') of a standard coated 17-10-13+ fertilizer product (mini granules) encapsulated with Resin A prepared in accordance with Example 4 herein, and a coated 17-10-13+ fertilizer product (mini granules) of the present invention (Sample D) encapsulated with Resin D prepared in accordance with Example 4 herein.
Figure 3:
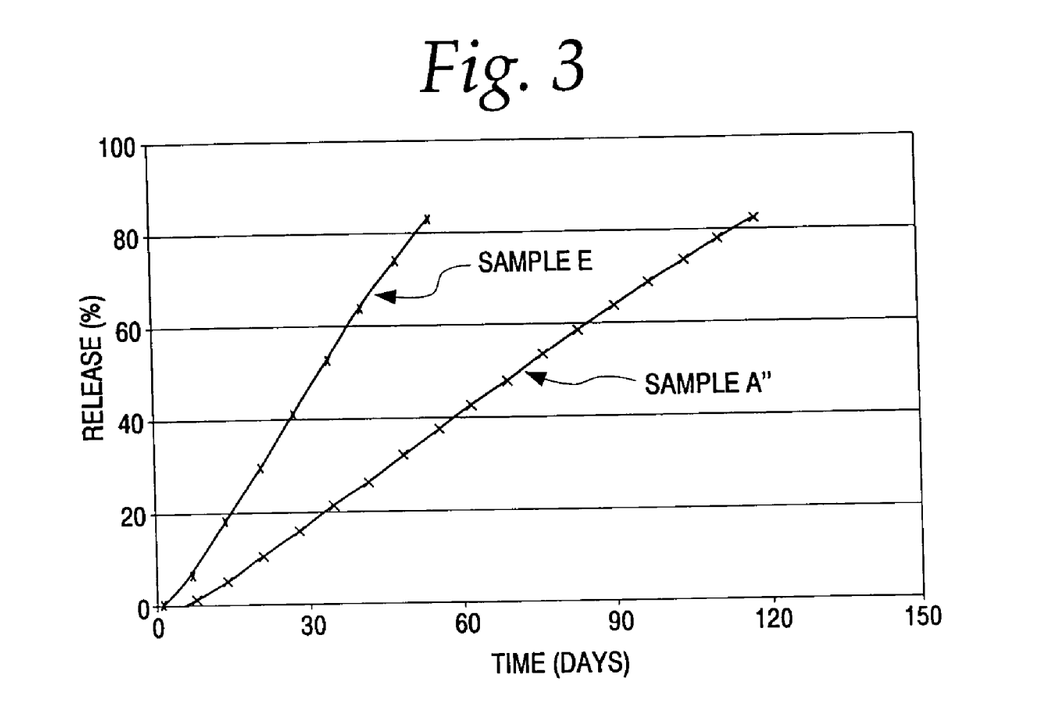
FIG. 3 illustrates a comparison of the nutrient release profile of a control sample (Sample A") of a standard coated 17-10-13+ fertilizer product encapsulated with Resin A prepared in accordance with Example 4 herein, and a coated 17-10-13+ fertilizer product of the present invention (Sample E) encapsulated with Resin E prepared in accordance with Example 4 herein.

The fertilizer products of Example 4 designated Sample A', Sample A", Sample D and Sample E were analyzed according to the waterleach test at 21° C. as described in Example 4. The release curves of these products are illustrated in FIGS. 2 and 3. As shown in FIGS. 2 and 3 the longevity of release of the CRF products in terms of the time between the time of application and the time at which at least about 75 wt % of core material was released from the products were as follows:

Sample A' (a control sample) was 100 days;

Sample D (a product in accordance with the present invention) was 30 days;

Sample A" (a control sample) was 110 days; and

Sample E (a product in accordance with the present invention) was 50 days.

Thus, from the tests conducted, it should be noted that CRF products produced in accordance with the present invention were found to demonstrate longevity of 60 days or less whereas the control samples were shown to have longevity significantly in excess of 60 days. The initial release period for each of the tested samples was shown to be be suppressed or inhibited within the first 24 hours after application so that less than 15 wt % of core material was released from the products in that time frame.

EXAMPLE 6

This example is to illustrate the use of the present invention for making a specific controlled release fertilizer product.

Figure 4:
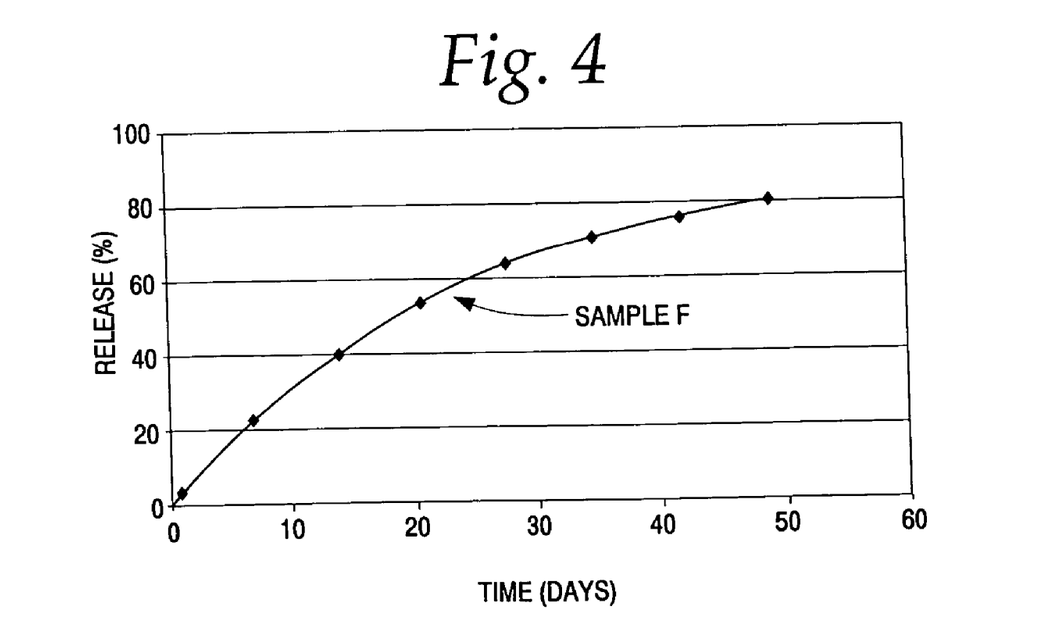
FIG. 4 illustrates the nutrient release profile of a 12-11-17+ fertilizer product (mini granules) of the present invention (Sample F) encapsulated with Resin B prepared in accordance with Example 6 herein.

A test sample product (identified herein as Sample F) in accordance with the present invention was prepared wherein an NPK mixture of mini granules with an overall N-P-K of 12-11-17+ was encapsulated with coating Resin B from Example 1 at a coating thickness of 23 $\mu$m according to the procedure described in Example 1. The release curve (as determined according to the waterleach test as described in Example 2) of the resulting product is shown in FIG. 4. From this figure it can be seen that the CRF product displayed a release profile wherein initial release of core material from the product was suppressed so that less than about 15 weight percent of core material was released from the product within a 24 hour period after application of the product and wherein longevity of release, at ambient temperature, between the time of application and the time at which at least about 75 weight percent of the core material is released from the product was 60 days or less and, specifically, about 42 days.

EXAMPLE 7

A greenhouse study was conducted to determine the agronomic benefits of the 12-11-17+ CRF product (Sample F of Example 6), and to compare the agronomic performance with current nursery-type industry standards. Samples of the 12-11-17+ fertilizer composition were applied at a rate of 1 kg/m$^3$ to Primula Obconica growing in 1 L pots. For purposes of comparison, samples of a industry standard water soluble 12-14-24+ fertilizer composition were applied at a rate of 1 kg/m$^3$ (grower's practice) to Primula Obconica. The performance of both applications was monitored and the agronomic benefits of the CRF 12-11-17+ fertilizer (Sample F) were clearly observable in that the plants were larger, had a better color and had a higher fresh weight.

EXAMPLE 8

Controlled release products according to the present invention having a suppressed initial release period and a predetermined longevity of 60 days or less can be formulated in accordance with the equation:

$$WVTR = \frac{\phi \cdot \delta}{\pi d^2}$$

wherein:

(i) WVTR is the water vapor transmission rate of the semi-permeable coating expressed in grams·$\mu$m/meters$^2$·day;

(ii) $\phi$ is the water diffusion rate (water flux) through the semi-permeable coating expressed in grams/day;

(iii) $\delta$ is the thickness of the coating layer expressed in $\mu$m; and (iv) d is the average diameter of the particulate core material expressed in meters.

Employing this equation in combination with other (fixed) parameters, such as the solubility of the core materials, the release of nutrients can be calculated by using an iterative model. Exemplary controlled release products coated with a single semi-permeable coating layer having the requisite water diffusion rate (water flux) through the semi-permeable coating ($\phi$) expressed in grams/day for a variety of combinations of coatings exhibiting various WVTR characteristics, having various granule core sizes and having various coating thicknesses are presented in the following table:

TABLE 3

| Controlled Release Product | WVTR (g·$\mu$m/m$^2$·day) | Average Granule Diameter (d) (m) | Coating Thickness ($\delta$) ($\mu$m) | Longevity @ 21° C. (days) |
|---|---|---|---|---|
| 1 | 800 | 0.003 | 35 | 61 |
| 2 | 1000 | 0.003 | 35 | 49 |
| 3 | 1200 | 0.003 | 35 | 41 |
| 4 | 1200 | 0.003 | 50 | 63 |
| 5 | 1500 | 0.003 | 35 | 33 |
| 6 | 1500 | 0.003 | 50 | 51 |

TABLE 3-continued

| Controlled Release Product | WVTR (g·μm/m²·day) | Average Granule Diameter (d) (m) | Coating Thickness (δ) (μm) | Longevity @ 21° C. (days) |
|---|---|---|---|---|
| 7 | 1500 | 0.003 | 65 | 62 |
| 8 | 2000 | 0.003 | 90 | 67 |
| 9 | 3000 | 0.003 | 110 | 54 |
| 10 | 800 | 0.002 | 20 | 28 |
| 11 | 800 | 0.002 | 35 | 44 |
| 12 | 800 | 0.002 | 45 | 53 |
| 13 | 800 | 0.002 | 50 | 63 |
| 14 | 1000 | 0.002 | 50 | 51 |
| 15 | 1200 | 0.002 | 50 | 42 |
| 16 | 2000 | 0.002 | 50 | 25 |
| 17 | 2000 | 0.002 | 80 | 32 |
| 18 | 2500 | 0.002 | 80 | 39 |

Although the invention has been described in its preferred forms with a certain degree of particularity, it is to be understood that the present disclosure has been made by way of example only. Numerous changes in the details of the compositions and in the methods of their preparation will be apparent without departing from the spirit and the scope of the invention, as defined in the appended claims.

What is claimed is:

1. A controlled release coated product in particulate form which is structured to provide a suppressed initial release period and a predetermined longevity comprising:
    (a) a particulate core material comprising a water soluble fertilizer composition; and
    (b) a single semi-permeable coating layer applied directly onto the surface of the particulate core material for controlling the release rate of the core material so that initial release of core material from the coated product is suppressed such that less than 15 weight percent of core material is released from the coated product within a 24 hour period after application of the coated product and longevity of release between the time of application and the time at which at least 75 weight percent of the core material is released from the coated product is 60 days or less at ambient temperature of about 21° C.; and
    (c) the single semi-permeable coating layer is formed from dicyclopentadiene ("DCPD") polymers which comprise a cyclo oil alkyd resin based on a natural oil selected from the group consisting of soybean oil and linseed oil, the DCPD polymers providing a uniform continuous polymeric film having a water vapor transmission rate (WVTR) greater than 800 g·μm/m²·day.

2. A process for producing a controlled release coated product in particulate form which is structured to provide a suppressed initial release period and a predetermined longevity comprising:
    (a) providing a particulate core material comprising a water soluble fertilizer composition; and
    (b) applying a single semi-permeable coating layer directly onto the surface of the particulate core material to enable the core material to release from the coated product at a rate wherein initial release of core material from the coated product is suppressed so that less than 15 weight percent of core material is released from the coated product within a 24 hour period after application of the coated product and wherein longevity of release between the time of application and the time at which at least 75 weight percent of the core material is released from the coated product is 60 days or less at ambient temperature of about 21° C.; the single semi-permeable coating layer being formed from a composition selected from the group consisting of thermoplastic and thermo setting polymers and resins which form a uniform continuous polymeric film having a water vapor transmission rate (WVTR) greater than 800 g·μm/m²·day.

3. The process of claim 2 wherein the thermoplastic and thermosetting polymers and resins are selected from the group consisting of vinyl resins, polyolefines; styrene-based polymers; acrylic polymers; polyesters, poly(oxy alkylene)s, cellulose derivatives, polyamides, polyamines; polycarbonates; polyimides; polysulfones; polysulfides; polysaccharides, polyester resins, epoxy resins; urethane resins; aminoplastics, and dicyclopentadiene ("DCPD") polymers.

4. The process of claim 3 herein the vinyl resins are selected from the group consisting of poly(vinyl acetate), poly(vinyl alcohol), poly(vinyl chloride), poly(vinylidene chloride), poly(vinyl pyrrolidone), poly(vinyl acetal) and poly(vinyl methylacetamide).

5. The process of claim 3 wherein the polyesters are selected from the group consisting of poly(alkylene terephthalate) and poly(caprolactone).

6. The process of claim 3 wherein the polyolefines are selected from the group consisting of polyethylene, polypropylene and polyisobutylene.

7. The process of claim 3 wherein the poly(oxy alkylene)s are selected from the group consisting of poly(ethylene oxide) and poly(propylene oxide).

8. The process of claim 3 wherein the cellulose derivatives are celluloseacetates.

9. The process of claim 2 for producing a coated product having a longevity of between 28 and 60 days.

10. The process of claim 2 for producing a coated product having a longevity of less than 28 days.

11. The process of claim 2 wherein the single semi-permeable coating layer has a thickness of about 20 to about 110 μm.

12. The process of claim 2 wherein the water soluble fertilizer composition comprises fertilizer granules.

13. The process of claim 2 wherein the particulate core material includes at least one secondary nutrient or micronutrient selected from the group consisting of calcium, sulfur, magnesium, iron, copper, zinc, manganese, boron, and molybdenum.

14. A process for producing a controlled release coated product in particulate form which is structured to provide a suppressed initial release period and a predetermined longevity comprising:
    (a) providing a particulate core material comprising a water soluble fertilizer composition; and
    (b) applying a single semi-permeable coating layer directly onto the surface of the particulate core material to enable the core material to release from the coated product at a rate wherein initial release of core material from the coated product is suppressed so that less than 15 weight percent of core material is released from the coated product within a 24 hour period after application of the coated product and wherein longevity of release between the time of application and the time at which at least 75 weight percent of the core material is released from the coated product is 60 days or less at ambient temperature of about 21° C.; the single semi-permeable coating layer being formed from dicyclo pentadiene ("DCPD") polymers which comprise a cyclo oil alkyd resin based on a natural oil selected from the group consisting of soybean oil and linseed oil, the DCPD polymers providing a uniform continuous polymeric film having a water vapor transmission rate (WVTR) greater than 800 g·m/m$^2$·day.

* * * * *